United States Patent [19]

Haber et al.

[11] Patent Number: 4,944,723
[45] Date of Patent: Jul. 31, 1990

[54] UNIVERSAL DISPOSABLE SAFETY SYRINGE SYSTEM

[75] Inventors: Terry M. Haber, El Toro; Clark B. Foster, Laguna Niguel; William H. Smedley, Lake Elsinore, all of Calif.

[73] Assignee: Habley Medical Technology Corporation, Laguna Hills, Calif.

[21] Appl. No.: 305,800

[22] Filed: Feb. 2, 1989

[51] Int. Cl.$^5$ .............................................. A61M 5/00
[52] U.S. Cl. ..................................... 604/110; 604/187; 604/195; 604/196; 604/228
[58] Field of Search ............... 604/110, 167, 184, 187, 604/195–196, 218, 220, 240, 243, 228, 203

[56] References Cited

U.S. PATENT DOCUMENTS

| | | | |
|---|---|---|---|
| 4,026,287 | 5/1977 | Haller | 604/195 |
| 4,507,117 | 3/1985 | Vining et al. | 604/228 |
| 4,692,156 | 9/1987 | Haller | 604/195 |
| 4,808,169 | 2/1989 | Haber et al. | 604/110 |
| 4,838,870 | 6/1989 | Haber et al. | 604/187 |

*Primary Examiner*—Stephen C. Pellegrino
*Assistant Examiner*—Michael Rafa
*Attorney, Agent, or Firm*—Morland C. Fischer

[57] ABSTRACT

A safety syringe having a double ended hypodermic needle cannula releasably retained at the distal bore of the syringe cylinder by a pair of jaws. A locking and positioning tip is attached to and movable reciprocally through the cylinder with a piston assembly. As the piston assembly is moved distally through the cylinder to expulse fluid therefrom, the proximal end of the cannula is deflected by and imbedded within the locking and positioning tip. The continued distal advancement of the piston assembly corespondingly drives the cannula and its jaws axially and outwardly from the distal bore of the cylinder, whereby the jaws release the cannula. When the piston assembly is moved proximally through the cylinder, the cannula is retracted within and shielded by the cylinder to avoid an accidental needle stick and render the syringe safe for handling and disposal.

25 Claims, 4 Drawing Sheets

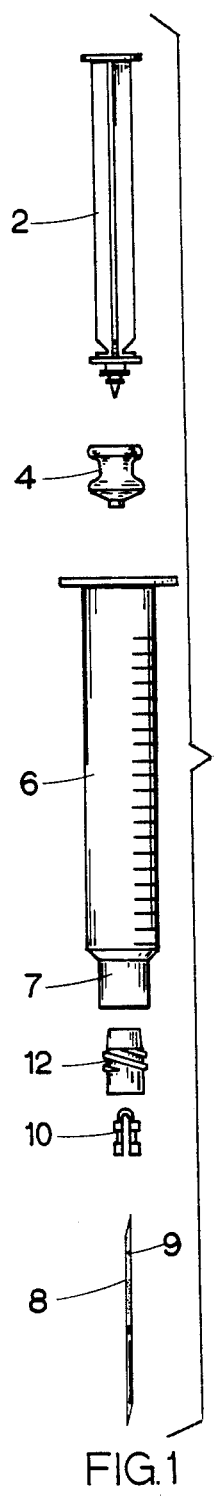
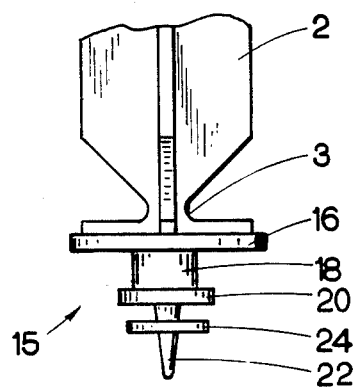
FIG.3
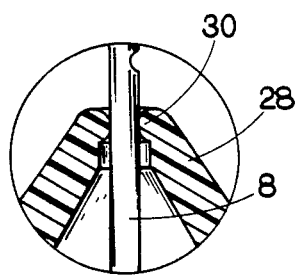
FIG.4
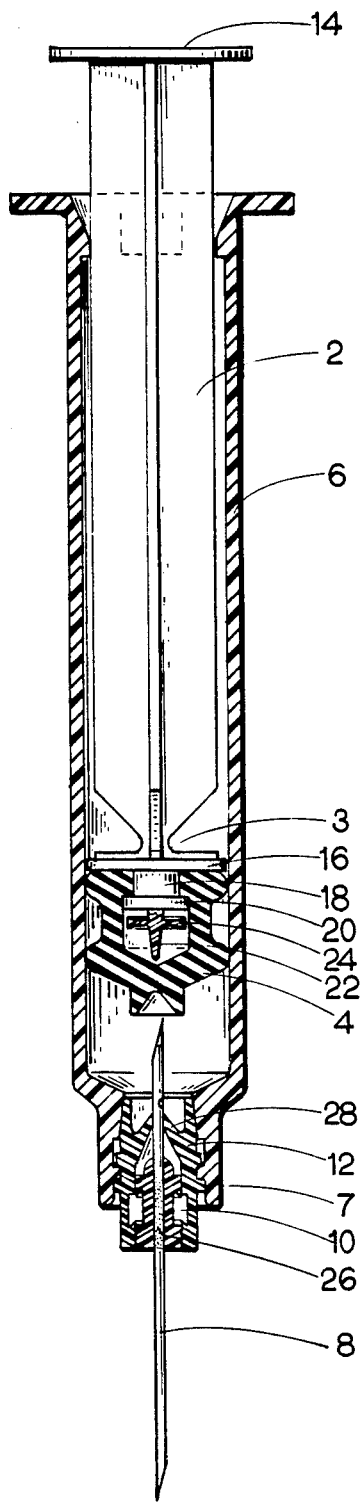
FIG.2
FIG.1

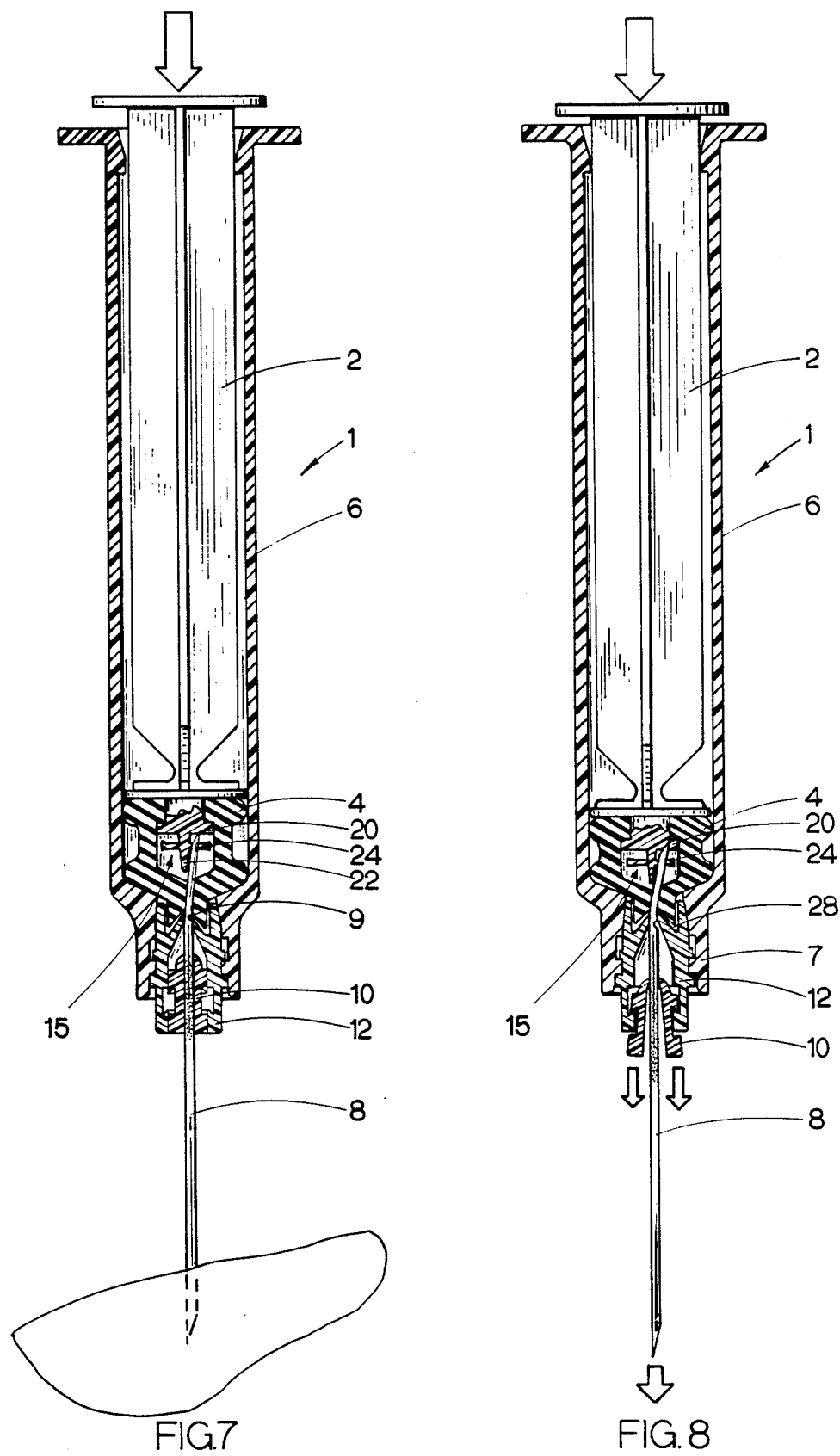

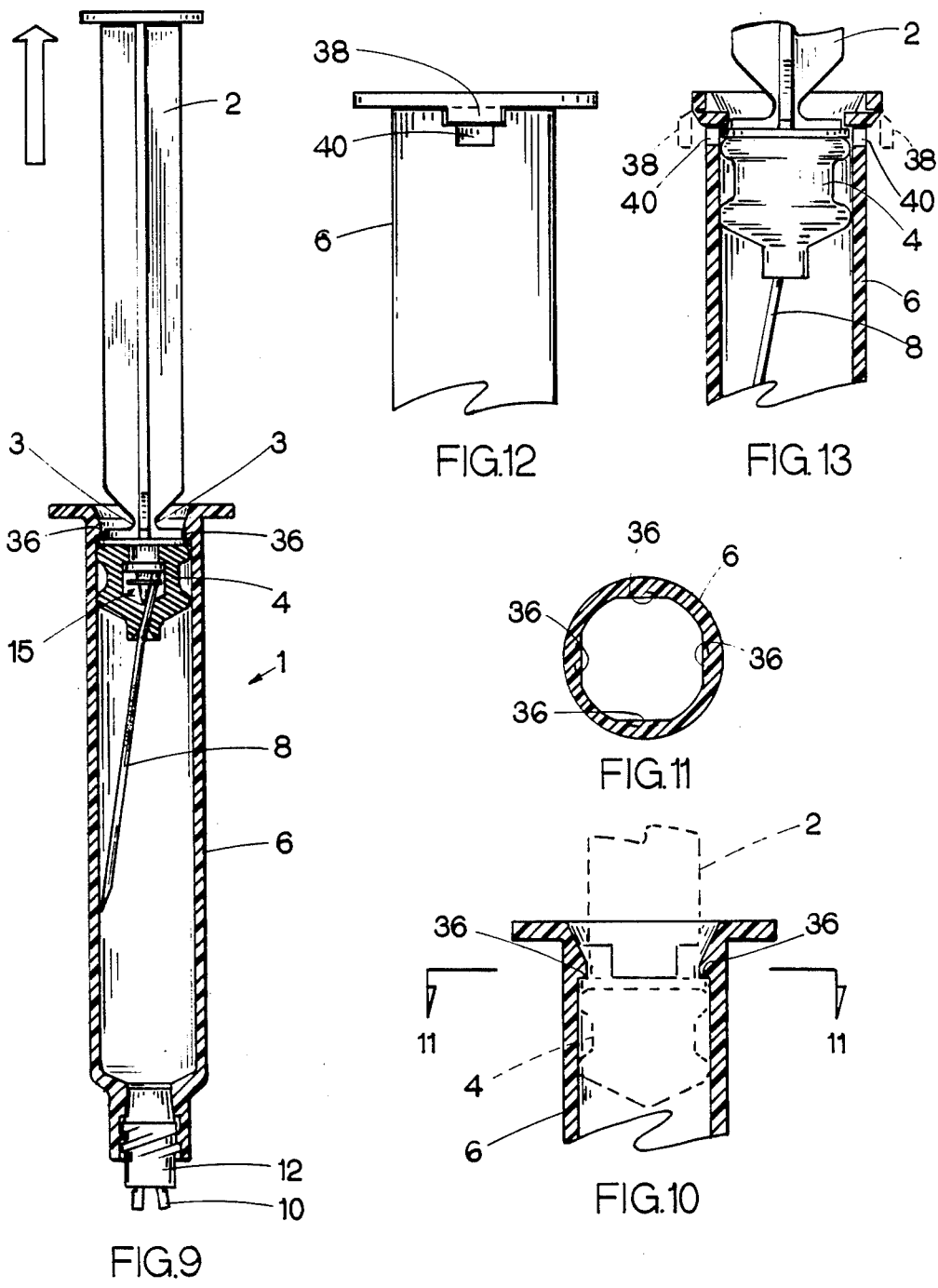

UNIVERSAL DISPOSABLE SAFETY SYRINGE SYSTEM

BACKGROUND OF THE INVENTION

1. Field of the Invention

This invention relates to a disposable safety syringe having a double ended hypodermic needle cannula which is engaged by a set of jaws and releasably retained at the distal bore of a syringe cylinder, and to means associated with a piston assembly for releasing the cannula from its engagement at the distal bore and retracting said cannula completely within the cylinder to form a compact package that is suitable for handling and disposal.

2. Background Art

Hypodermic syringes are used for a variety of injection procedures including the delivery of medicinal drugs to a recipient. However, once the injection procedure is completed and the syringe cylinder emptied, problems may arise as a consequence of failing to properly and adequately dispose of the syringe. By way of the first example, the syringe may be used to treat a patient having a communicable disease. To prevent reuse, the hypodermic needle is sometimes broken before the syringe is discarded. Health care workers are susceptable to accidental and potentially infectious needle sticks due to the careless handling of the hypodermic needle when breaking the needle or disposing of the syringe after use. The resulting mini-accidents caused by an accidental needle stick typically requires a blood test for such diseases as AIDS and hepatitis. The corresponding cost and inefficiency of testing health care workers who have received an inadvertent needle stick result in considerable waste, which may be particularly damaging to a health care facility striving for economy and efficiency. By way of a second example, drug abusers have been known to rummage through the trash of a health care facility in an effort to find empty syringes which have been discarded after use. Such syringes are often used in an illicit capacity, whereby to promote drug abuse and the possible spread of disease.

One example of a syringe having a hypodermic needle cannula that may be retracted within a cylinder and canted relative to the longitudinal axis of said cylinder is available by referring to U.S. Pat. No. 4,804,370 issued Feb. 14, 1988 and assigned to the assignee of this patent application.

One example of a syringe having a hypodermic needle cannula that is releasably retained at the distal bore of the syringe cylinder by a set of jaws is available by referring to U.S. Pat. No. 4,808,169 issued Jan. 28, 1989 and assigned to the assignee of this patent application.

SUMMARY OF THE INVENTION

In general times, this invention relates to a disposable safety syringe of the type including a fluid filled cylinder and a double ended hypodermic needle cannula having a proximal end extending into the cylinder to communicate with the fluid thereat and a distal end extending axially from the cylinder for penetrating a targeted tissue area. The needle cannula is releasably and frictionally engaged by a pair of jaws, and the jaws are received within and slidable through a collar. In the assembled relationship, the collar is connected to the cylinder at the distal bore thereof to retain the jaws and cannula thereat. As an advantage of the present invention, a single size cylinder is adapted to be interfaced with different cannulas, jaws and collars to reduce manufacturing costs and increase efficiency.

A piston assembly is movable axially and reciprocally through the cylinder. The piston assembly includes a relatively thin walled, hollow piston and an elongated piston stem. A locking and positioning tip is coextensively connected to the piston stem within the hollow piston. The locking and positioning tip comprises a needle deflecting cone aligned axially with the needle cannula and a pair of surfaces coaxially aligned with and spaced from one another along the cone. A first of said surfaces is adapted to be penetrated by a needle cannula, while the second surface is substantially impenetrable.

In operation, and during an injection, the piston assembly is moved distally through the cylinder to expulse fluid therefrom via the needle cannula. The piston assembly is moved distally through the cylinder until the proximal end of the cannula pierces the hollow piston and contacts the locking and positioning tip of the piston stem. Accordingly, the proximal end of the cannula is deflected or bent by the needle deflecting cone. A further distal movement of the piston assembly causes the bent proximal cannula end to penetrate the first needle penetrable surface and become imbedded within the second needle impenetrable surface of the locking and positioning tip, whereby the needle cannula is fixedly and reliably attached to the piston assembly at said locking tip. Therefore, any further distal advancement of the piston assembly is transferred to the cannula to cause the cannula and the jaws thereof to slide axially and outwardly from the collar and past the distal bore of the cylinder. The cannular is released by the jaws when said jaws are moved outwardly from the cylinder. Thereafter, when the piston assembly is moved proximally through the cylinder, the cannula is movable therewith so as to be retracted within and surrounded by the cylinder to form a compact package suitable for safe handling and disposal while avoiding an accidental needle stick and the spread of a possibly contagious and life threatening disease.

BRIEF DESCRIPTION OF THE DRAWINGS

FIG. 1 shows an exploded view of the disposable safety syringe which forms the present invention;

FIG. 2 is a partial cross-sectional view of the safety syringe of FIG. 1 in the assembled configuration;

FIG. 3 is a detailed illustration of a locking and positioning tip that is formed at a piston stem of the syringe of FIG. 2;

FIG. 4 is an enlarged detail of a cannula supporting and sealing flange of the syringe of FIG. 2;

FIG. 7 illustrates the syringe in the post-injection state after an injection has been administered;

FIG. 8 shows the syringe with the needle cannula thereof being axially advanced and released from a set of jaws at the distal bore of the syringe cylinder;

FIG. 9 shows the syringe with the needle cannula thereof being retracted completely within and surrounded by the syringe cylinder;

FIGS. 10 and 11 are illustrative of a preferred embodiment of the invention for preventing the removal of the piston assembly from the open proximal end of the syringe cylinder; and FIGS. 12 and 13 are illustrative of another preferred embodiment of the invention for preventing the removal of the piston assembly from the open proximal end of the syringe cylinder.

DESCRIPTION OF THE PREFERRED EMBODIMENT

Figure 5:
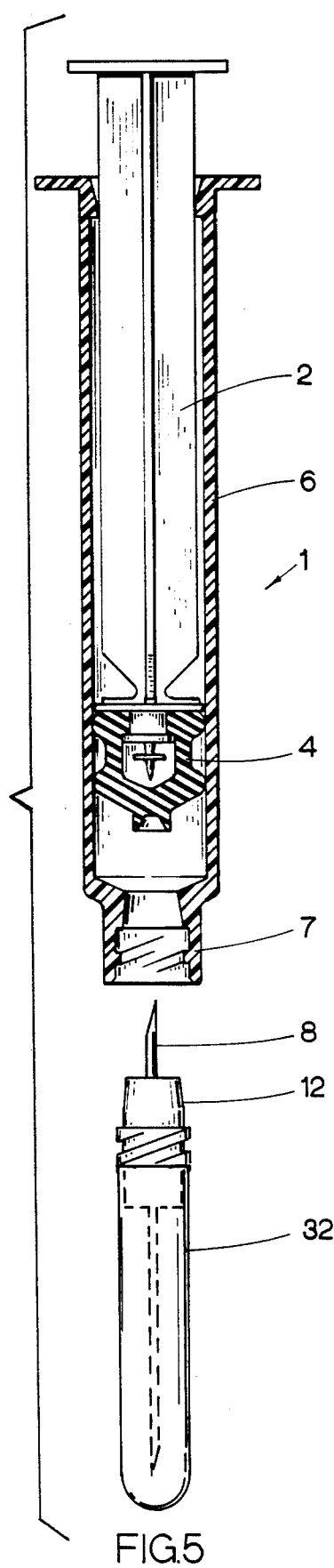
FIG. 5 illustrates the disposable safety syringe of the present invention in the as-package configuration.

The disposable safety syringe which forms the present invention is best described while referring to the drawings, where FIGS. 1 shows an exploded view of the syringe 1. Syringe 1 includes an elongated piston stem 2 which carries a relatively thin walled, generally hollow, and deformable piston 4 through a cylinder or barrel 6 having an open proximal end and a relatively narrow distal bore 7. A double ended hypodermic needle cannula 8 having a fluid orifice 9 extending therethrough is to be received between a pair of axially slidable and spring-like jaws 10. As well soon be explained, the jaws 10 are releasably engaged at a tight friction fit within a cylindrical, threaded collar 12 so as to cause said jaws to rotate into clamping engagement with and thereby frictionally retain the needle cannula 8 at the distal end of cylinder 6. The screw threaded collar 12 is adapted to be mated to corresponding screw threads of formed in the distal bore 7 of cylinder 6 so that the needle cannula 8 can communicate fluidically with the contents of said cylinder to permit an injection of the contents. It is to be understood that cylinder 6 is of suitable configuration to receive different sized cannulas, jaws, and collars, depending upon the application of the syringe, whereby the advantages of this invention may be realized with a universal cylinder to, thereby, minimize manufacturing costs and design considerations.

The details of the syringe 1 in the assembled, condition are described while referring to FIGS. 2-4 of drawings. The piston stem 2, which is received within and moved reciprocally through the syringe cylinder 6, includes a proxmial flange 14 by which the movement of the stem 2 through the cylinder 6 may controlled. The piston stem 2 has a scored after 3 of reduced cross-section, the advantage of which will be described in greater detail when referring to FIG. 9. Located at the distal end of piston stem 2 is a (e.g. plastic) locking and positioning tip 15 by which the stem may be reliably interconnected with piston 4 to form a piston assembly. The locking tip 15 is also adapted to be moved into fixed engagement with the proximal end of needle cannula 8 so that said cannula can be rendered non-reusable and retracted within the cylinder 6 to permit syringe 1 to be safely disposed of after use.

More particularly, and referring concurrently to FIGS. 2 and 3, a piston support base 16 extends across the distal end of the piston stem 2 to receive thereagainst and provide axial support for the hollow piston 4. That is, an axially directed force applied to the piston stem 2 for moving the piston assembly distally through cylinder 6 is transferred to piston 4 at the support base 16. Coextensively connected to and projecting from support base 16 is a cylindrical spacer 18. Spaced distally from the support base 16 by means of spacer 18 is a relatively thick needle limiting surface 20. Needle limiting surface 20 is of suitable size to be received within the hollow body of the piston 4 so that the piston can be attached to the piston stem 2 for completing the piston assembly. Moreover, and as will be described in greater detail hereinafter when referring to FIGS. 7 and 8, surface 20 is of suitable composition and thickness to limit the axial movement and penetration of needle cannula 8 therethrough when the locking tip 15 of piston stem 2 is advanced through cylinder 6 and moved into contact with the proximal end of cannula 8 after an injection has been administered. Projecting outwardly and axially from the needle limiting surface 20 is a needle deflecting cone 22. Needle deflecting cone 22 forms the distal end of the locking and positioning tip 15 of piston stem 2. As will also be described in greater detail when referring to FIGS. 7 and 8, needle deflecting cone 22 is, in the assembled configuration, axially aligned with the needle cannula 8 so as to engage and deflect the proximal end of said cannula when locking tip 15 is advanced through cylinder 6 and moved into contact with the cannula. Coextensively connected to deflecting cone 22 and spaced distally from the needle limiting surface 20 is relatively thin, disk-like needle gripping and positioning surface 24. Gripping and positioning surface 24 is of suitable composition and thickness to be completely penetrated by the proximal end of needle cannula 8 such that said cannula may be received at and embedded within the needle limiting surface 20.

In the assembled configuration of FIG. 2, the jaws 10 which frictionally retain cannula 8 are releasably received within and frictionally engaged by the collar 12, and such collar is screw threaded into mating engagement with the syringe cylinder 6 at the distal bore 7 thereof to lock cannula 8 at the distal bore 7 of syringe 1. The retention of cannula 8 by the jaws 10 may be enhanced by providing the cannula with a raised or textured, high friction surface 26. Thus, the proximal end of cannula 8 extends into cylinder 6 in fluid communication therewith, and the distal end of cannula 8 extends axially and outwardly from the distal bore 7 for penetrating the tissue of a patient. However, and as will be explained in greater detail hereinafter when referring to FIG. 8, the cannula 8 and jaws 10 are slidable axially and distally relatively to collar 12 release the clamping engagement of cannula 8 by jaws 10, whereby the cannula is free to be retracted within cylinder 6 to permit a safe and non-reusable disposal of the syringe 1.

Needle cannula 8 is also frictionally engaged by the collar 12 to accurately retain the cannula in in alignment with cylinder 6 and the locking and positioning tip 15 of piston stem 2. More particularly, and referring to FIGS. 2 and 4, the collar 12 is provided with a radially inward extending support flange 28 which surrounds cannula 8. The support flange 28 frictionally engages the cannula at an annular or torroidal lip 30 which forms a fluid tight seal between the support flange 28 and cannula 8 within the distal bore 7 to prevent leakage from the cylinder 6. It might be noted that the fluid seal formed by lip 30 is integral with the collar 12 and not with the cylinder 6, whereby to enhance the reliability of said seal.

The syringe 1 is shown in FIG. 5 of the drawings in the as-packaged configuration before the needle cannula 8 is connected to the cylinder and locked at the distal bore 7. In the as-packaged configuration, it is desirable that piston stem 2 be initially located within the cylinder 6 so that the piston 4 is spaced proximally from the distal bore 7 to prevent the cannula 8 from penetrating the piston during the installation of the cannula. The cannula 8 is pre-assembled with the jaws 10 (of FIG. 2) and collar 12, and the assembly is carried within a shielded housing 32 to preserve the sterility of the cannula and prevent an accidental needle stick. With the proximal end of cannula 8 exposed to communicate with the cylinder 6, the screw threaded collar 12 is rotated into mating engagement with the distal bore 7 at the corresponding screw threads thereof. The shielded housing 32 may then be removed to expose the distal end of cannula 8 and allow communication between the cylinder and a source of fluid via said cannula.

Figure 6:
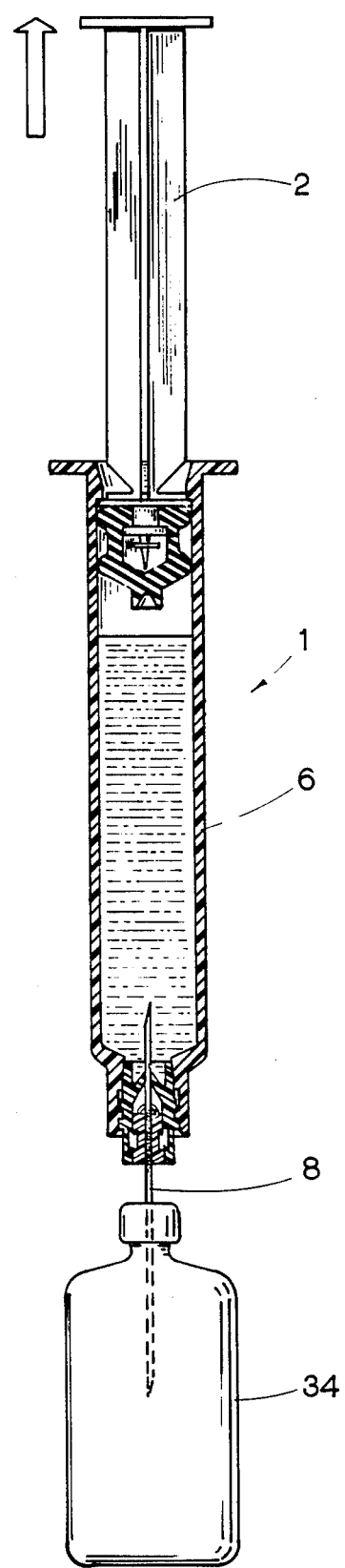
FIG. 6 shows the safety syringe in the pre-injection state being infused with a supply of fluid.

FIG. 6 of the drawings shows the syringe 1 in the pre-injection state with the cylinder 6 being infused with fluid in a medically accepted fashion. That is, the distal end of the needle cannula is moved into communication with a source 34 of fluid (e.g. medication, or the like). The piston stem 2 is then withdrawn proximally through the cylinder 6 (in the direction of the reference arrow), whereby fluid is drawn from the source 34 into cylinder 6 via cannula 8 so that the syringe 1 is ready for the administration of an injection.

FIG. 7 of the drawings shows the syringe 1 in the post-injection state after fluid has been expulsed from the cylinder 6 to a targeted tissue area of a patient. More particularly, the piston stem 2 is removed distally through the cylinder 6 (in the direction of the reference arrow), whereby to correspondingly drive the piston 4 towards the needle cannula 8. As piston 4 is advanced through the cylinder 6, the proximal end of the needle cannula, which projects into the cylinder, will pierce the piston. When piston 4 is pushed to the distal aspect of cylinder 6, and while said cannula 8 is still firmly retained between the jaws 10 within the collar 12, the cannula 8 is deflected and bent by the needle deflecting cone 22 of the locking and positioning tip 15 at the hollow interior of piston 4. The fluid orifice 9 of cannula 8 functions as a point of structural weakness and thereby encourages bending of the cannula thereat. Thus, the proximal end of the cannula 8 rotates at orifice 9 and penetrates the relatively thin needle gripping and positioning surface 24 of locking tip 15.

In FIG. 8 of the drawings, the piston stem 2 is advanced further through the syringe cylinder 6 (in the direction of the reference arrow) to compress the deformable piston 4 against the relatively narrow distal bore 7. More particularly, with piston 4 already located at the distal aspect of cylinder 6 (as shown in FIG. 7), the continued distal relocation of piston stem 2 through cylinder 6 correspondingly drives piston 4 into contact with the distal bore 7, where said piston is compressed. The distal advancement of the locking and positioning tip 15 of piston stem 2 and the axial compression of piston 4 causes the bent proximal end of needle cannula 8 to become imbedded within and fixedly attached to the relatively thick needle limiting surface 20.

With the proximal end of needle cannula 8 penetrating the needle gripping and positioning surface 24 and embedded within the needle limiting surface 20, the cannula is permanently secured to locking tip 15. Therefore, any further distal relocation of the piston stem 2 through cylinder 6 is transferred to the cannula 8 by way of locking tip 15. Accordingly, the cannula is pushed axially and distally (in the direction of the reference arrow) relative to the distal bore 7. The distal movement of cannula 8 results in a corresponding movement of the jaws 10 relative to the collar 12. That is to say, the distal movement of cannula 8 through distal bore 7 causes the jaws 10 to overcome their frictional engagement by and slide axially through collar 12. Thus, the jaws 10 slide distally and outwardly (in the direction of the reference arrows) from the collar 12 so as to automatically rotate out of engagement with and thereby release the cannula 8. At this time, the cannula 8 is retained only at the proximal end thereof by the locking and positioning tip 15 of piston stem 2 and the support flange 28 of the collar 12.

FIG. 9 of the drawings shows the syringe 1 with the needle cannula 8 retracted within the cylinder 6 so that the syringe can be rendered non-reusable and safe for handling and disposal. More particularly, after the jaws 10 have been pushed distally and outwardly relative to collar 12 to release the cannula 8 therebetween, the piston stem 2 is relocated proximally (in direction of the reference arrow) through cylinder 6. The proximal relocation of stem 2 correspondingly withdraws the piston 4 and the locking and positioning tip 15 rearwardly through the cylinder 6. Inasmuch as needle cannula 8 is fixedly attached to the locking tip 15 of piston stem 2, as previously disclosed, the proximal withdrawal of locking tip 15 causes the cannula 8 to also be retracted into the cylinder 6. That is, the axial force generated with piston stem 2 is relocated proximally through cylinder 6 overcomes the frictional engagement of cannula 8 by support flange 28 of collar 12 and permits the cannula to be retracted completely within and shielded by the cylinder 6. Moreover, the bent proximal end of cannula 8 and the mechanical stresses that are induced therein combine to cant the distal end of said cannula, whereby to prevent a return of the cannula from the retracted position (of FIG. 9) to the axially extended position (of FIG. 2) in the event that the piston stem 2 is moved axially and distally through the cylinder, whereby to prevent reuse of the syringe and avoid an accidental needle stick and the spread of a contagious and possibly life threatening disease.

What is more, and as additional advantage of the present invention, the proximal end of the cylinder 6 may include suitable stop means by which to permit the removal of the piston through the open proximal end of the cylinder and thereby block access to the needle cannula 8 after use. More particularly, and referring concurrently to FIGS. 9-11 of the drawings where one preferred stop means is illustrated, the cylinder 6 is provided with a series of radially and inwardly extending flanges or flats 36. The flats 36 form areas of reduced diameter around the periphery of cylinder 6 below the open proximal end thereof. Accordingly, the radially inward extending flats 36 will engage and block the withdrawal of the piston 4 from the cylinder 6 as the piston stem is moved proximally therethrough, whereby the cannula 8 is irretrievably located within said cylinder. With the piston stem 2 completely withdrawn from the cylinder 6 (as best shown in FIG. 9), the stem may be rotated and broken at the scored region 3 thereof and discarded to render syringe 1 in a totally non-reusable condition that is suitable for a safe disposal.

FIGS. 12 and 13 of the drawings show another preferred stop means by which to prevent the removal of the piston 4 through the open proximal end of the cylinder 6 to thereby block access to the needle cannula after use. More particularly, a pair of tabs 38 are integrally connected at opposite sides of the cylinder 6 below the open proximal end thereof. During manufacture, the cylinder is molded with the tabs (shown in phantom) arranged in spaced parallel alignment to the cylinder. Each tab 38 is adapted to be bent inwardly around an integral hinge and rotated into a respective T-shaped slot 40 that is formed through the cylinder 6. When received within their slots 40, the tabs 38 project radially inward into the cylinder 6 to block the withdrawal of the piston 4 from the cylinder as the piston stem is moved proximally therethrough, in much the same way as the flats 36 of FIGS. 10 and 11 engage piston 4 to block the removal thereof.

It should now be apparent that, by virtue of the present invention, the canted needle cannula 8 cannot be removed from the cylinder 6 and the syringe 1 cannot be reused. More particularly, the cannula 8 cannot be removed form the open proximal end of the cylinder 6, because the stop means (of FIGS. 9-13) prevent the movement of the piston 4 therepast. What is more, access to the interior of the cylinder 6 is also blocked so that the cannula 8 is completely shielded by the cylinder and rendered irretrievable therewithin. Accordingly, a disposal cartridge is created so that the syringe 1 may be safely handled and discarded while avoiding an accidental needle stick and the possible spread of a contagious disease.

It will be apparent that while a preferred embodiment of the invention has been shown and described, various modifications and changes may be made without departing from the true spirit and scope of the invention. For example, while a pair of coaxially aligned needle surfaces 20 and 22 are shown to comprise the needle locking and positioning tip 15 of piston stem 2, this is not to be regarded as a limitation of the invention, and said locking tip 15 may have any number of needle surfaces by which said cannula is to be fixedly connected to and movable with the piston stem 2.

Having thus set forth a preferred embodiment of the invention, what is claimed is:

1. A syringe comprising:
   a cylinder having proximal and distal ends and receiving a supply of fluid at the interior thereof;
   piston assembly means movable reciprocally through said cylinder;
   a hypodermic needle cannula communicating with the fluid supply of said cylinder and projecting outwardly from the distal end of said cylinder for penetrating a targeted tissue area;
   clamping means comprising at least one pair of normally open jaws between which said needle cannula is received, said jaws located within and closed by the distal end of said cylinder for releasably retaining said needle cannula at said distal end; and
   means connected to and movable distally with said piston assembly means through said cylinder for sliding said jaws relative to the distal end of said cylinder and thereby causing said jaws to open and release said needle cannula from said distal end.

2. The syringe recited in claim 1, further comprising means for retracting said needle cannula proximally into said cylinder after said jaws have released said cannula from the distal end of said cylinder.

3. The syringe recited in claim 2, wherein said means for retracting said needle cannula is attached to and movable proximally with said piston assembly means.

4. The syringe recited in claim 3, further comprising means for preventing the removal of said piston assembly means from the proximal end of said cylinder when said piston assembly means is moved proximally through said cylinder to retract said cannula therewithin.

5. The syringe recited in claim 4, wherein said means for preventing the removal of said piston assembly means comprises stop means extending radially and inwardly from said cylinder to engage said piston assembly means and thereby block the removal thereof.

6. The syringe recited in claim 4, wherein said means for preventing the removal of said piston assembly means comprises at least one tab hingedly connected to said cylinder at the exterior thereof and an opening formed through said cylinder, said tab being rotatable through said opening to extend radially into said cylinder to form a stop for engaging said piston assembly means and thereby blocking the removal thereof.

7. The syringe recited in claim 3, wherein said piston assembly means includes at least one needle penetrable surface, and
   said needle cannula has proximal and distal ends, said proximal cannula end being in alignment with said needle penetrable surface at the interior of said syringe cylinder so as to penetrate said surface and thereby be connected to said piston assembly means when said piston assembly means is moved distally through said cylinder, said needle cannula being retracted into said cylinder when said piston assembly means is moved proximally through said cylinder after said cannula has penetrated said needle penetrable surface.

8. The syringe recited in claim 7, wherein said piston assembly means comprises a piston stem attached to a piston of hollow construction, said needle penetrable surface located at the hollow interior of said piston.

9. The syringe recited in claim 1, further comprising a collar connected within said cylinder at the distal end thereof so as to surround said pair of jaws and retain said jaws at said distal end, said jaws being slidable through said collar and outwardly from the distal end of said cylinder for releasing said needle cannula from said distal end.

10. The syringe recited in claim 1, wherein said needle cannula has proximal and distal ends, said distal cannula end projecting outwardly from the distal end of said cylinder and said proximal cannula end projecting into the interior of said cylinder to communicate with the fluid supply thereof; and
    the means attached to and movable with said piston assembly means for displacing said jaws relative to the distal end of said cylinder is a needle impenetrable surface movable towards and into contact with said proximal cannula end at the interior of said cylinder when said piston assembly means is moved distally therethrough, said needle impenetrable surface pushing said cannula and said jaws outwardly from said distal cylinder end for causing said jaws to release said cannula.

11. The syringe recited in claim 11, further comprising means for bending said needle cannula and thereby deflecting the proximal end thereof into alignement with the needle impenetrable surface of said piston assembly means, so that said needle impenetrable surface is moved into contact with said proximal cannula end when said piston assembly means is moved distally through said cylinder.

12. The syringe recited in claim 11, wherein said needle cannula include a fluid orifice located within said cylinder to receive fluid from the supply thereof and to form an area of structural weakness at which said cannula is bent.

13. The syringe recited in claim 11, wherein said means for bending said needle cannula and deflecting the proximal end thereof is a conically shaped tip attached to said piston assembly means and coaxially aligned with and projecting distally from said needle impenetrable surface.

14. A syringe comprising:
   a cylinder having proximal and distal ends to receive a supply of fluid at the interior thereof;
   piston assembly means movable reciprocally through said cylinder;
   a double ended hypodermic needle cannula having a proximal end projecting inwardly of said cylinder to communicate fluidically with the contents thereof and a distal end projecting outwardly of said cylinder to administer an injection of the contents;
   means for releasably retaining said needle cannula at the distal end of said cylinder; and
   piston assembly means movable distally through said cylinder for contacting the proximal end of said cannula and pushing said cannula distally relative to said cylinder and outwardly from said cannula retaining means, whereby said cannula may be removed from the distal end of said cylinder,
   said piston assembly means having a needle impenetrable surface within which the proximal end of said needle cannula is embedded so that said cannula will be pushed distally when said piston assembly means is moved distally through said cylinder and into contact with the proximal end of said cannula and a needle penetrable surface spaced distally from said needle impenetrable surface for receiving the proximal end of said cannula therethrough so that said cannula will be affixed to said piston assembly means when said piston assembly means is moved distally through said cylinder and into contact with the proximal end of said cannula.

15. The syringe recited in claim 14, wherein said locking means also includes a needle deflecting tip coaxially aligned with and extending distally of said needle penetrable surface, said needle deflecting tip contacting the proximal end of said needle to thereby bend said proximal end and deflect said proximal end towards said needle penetrable surface when said piston assembly means is moved distally through said cylinder.

16. The syringe recited in claim 14, wherein said piston assembly means comprises an elongated piston stem and hollow, needle penetrable piston, said needle impenetrable and penetrable surfaces located at the interior of said hollow piston.

17. The syringe recited in claim 14, wherein said means for releasably retaining said cannula at the distal end of said cylinder is a set of jaws which are received within and movable through said distal end, said jaws being moved outwardly of said distal cylinder end with said cannula for releasing said cannula to be removed from said distal end when said cannula is pushed distally relative to said cylinder.

18. The syringe recited in claim 17, further comprising a collar located within the distal end of said cylinder and surrounding said jaws for releasably retaining said jaws within said distal cylinder end and thereby releasably retaining said cannula, said jaws being slidable through said collar so as to be moved outwardly of said cylinder when said cannula is pushed distally relative to said cylinder.

19. syringe comprising:
   a cylinder having proximal and distal ends and receiving a supply of fluid at the interior thereof;
   piston assembly means movable reciprocally through said cylinder;
   a hypodermic needle cannula having sharpened proximal and distal ends, said proximal end extending into said cylinder to communicate with the fluid supply thereof and said distal end projecting outwardly from said cylinder to penetrate a targeted tissue area;
   normally open clamping means located within and closed by the distal end of said cylinder for releasably retaining said needle cannula at said distal cylinder end; and
   a needle impenetrable surface carried by and movable distally with said piston assembly means through said cylinder and into contact with the sharpened proximal end of said needle cannula for pushing said cannula and displacing said claimping means distally and outwardly from the distal end of said cylinder for causing said clamping means to open and release said cannula from said distal cylinder end.

20. The syringe recited in claim 19, further comprising means carried by said piston assembly means for bending said needle cannula and thereby deflecting the proximal end thereof towards said needle impenetrable surface, so that said needle impenetrable surface is moved into contact with said deflected proximal cannula end when said piston assembly means is moved distally through said cylinder.

21. The syringe recited in claim 20, wherein said needle cannula includes a fluid orifice located within said cylinder to receive fluid from the supply thereof and to form an area of structural weakness at which said cannula is bent.

22. The syringe recited in claim 20, wherein said means for bending said needle cannula and deflecting the proximal end thereof is a conically shaped tip carried by said piston assembly means and projecting distally and ahead of said needle impenetrable surface.

23. The syringe recited in claim 20, further comprising a needle penetrable surface carried by said piston assembly means and located between said needle, cannula bending means and said needle impenetrable surface, such that the proximal end of said needle cannula which is deflected by said bending means towards said impenetrable surface is passed through said needle penetrable surface to become interconnected with said piston assembly means when said piston assembly means is moved distally through the cylinder, said needle cannula being retracted into said cylinder when said piston assembly means is moved proximally through said cylinder after said cannula has passed through said needle penetrable surface and said clamping means has released said cannula.

24. The syringe recited in claim 23, when said needle bending means, said needle penetrable surface, and said needle impenetrable surface are integrally connected and coaxially aligned with one another.

25. The syringe recited in claim 19, wherein said clamping means comprises at least one pair of jaws which is received within and slidable relative to the distal end of said cylinder, said cannula being releasably secured between said pair of jaws when said jaws are located within said distal end.

* * * * *